(12) United States Patent
Baumgartner

(10) Patent No.: US 6,350,582 B1
(45) Date of Patent: *Feb. 26, 2002

(54) HAIR ANALYSIS METHOD

(75) Inventor: Werner Andreas Baumgartner, Malibu, CA (US)

(73) Assignee: Psychemedics Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/499,490

(22) Filed: Feb. 7, 2000

Related U.S. Application Data

(60) Division of application No. 08/813,376, filed on Mar. 6, 1997, now Pat. No. 6,022,693, which is a continuation-in-part of application No. 07/737,703, filed on Jul. 30, 1991, which is a continuation-in-part of application No. 07/285,123, filed on Dec. 16, 1988, now Pat. No. 5,324,642, which is a continuation-in-part of application No. 07/215,591, filed on Jul. 6, 1988, now abandoned, which is a continuation-in-part of application No. 07/138,515, filed on Dec. 28, 1987, now abandoned.

(51) Int. Cl.$^7$ .................. G01N 33/53; G01N 33/531; G01N 33/567; C12Q 1/37

(52) U.S. Cl. .................. 435/7.1; 435/23; 435/24; 435/961; 435/962; 435/265; 435/267; 436/504; 436/542; 436/543; 436/804; 436/816

(58) Field of Search .................. 435/7.1, 23, 24, 435/961, 962, 265, 267, 963; 436/504, 542, 543, 804, 816, 825, 901

(56) References Cited

U.S. PATENT DOCUMENTS 5,324,642 A * 6/1994 Baumgartner ............... 435/7.1
5,466,579 A * 11/1995 Baumgartner ............... 435/7.1
6,022,693 A * 2/2000 Baumgartner ............... 435/7.1

OTHER PUBLICATIONS

Shih. Disseration Abstracts International, vol. 49/11–B, 1988.*

Gnonlonfoun et al. J. Inorg. Biochem. 42:207–215, abstract, 1991.*

Yang et al. Int. J. Peptide & Protein Res. 48:532–538, abstract, 1996.*

Hochuli et al. Bio/Technology 6:1321–1325, 1988.*

Martinez et al. Biochem. Biophys. Res. Commun. 182:92–98, abstract, 1992.*

Polatnick et al. Arch. Virol. 84/3–4:269–275, abstract, 1985.*

* cited by examiner

*Primary Examiner*—S. Devi
(74) *Attorney, Agent, or Firm*—Dewey Ballantine LLP

(57) ABSTRACT

A method for the direct analysis of the presence of an analyte which becomes embedded in keratinized structures, e.g., hair, fingernails and toenails, from the bloodstream of a subject which comprises preparing a mixture containing dithiothreitol or dithioerythritol ("DTT"), an enzyme suitable for the digestion of the keratin structure and a sample of the keratin structure; permitting the enzyme to digest the sample of keratin structure to form a digest solution, followed by the addition of a salt of a metal of copper, zinc, manganese, iron, lead, cadmium, mercury, silver and cobalt to deactivate the DTT; and finally subjecting the digest solution to analysis to determine the presence of the analyte in the keratin structure sample. The protease enzymes papain, chymopapain, and proteinase K are preferred for use in the invention.

4 Claims, No Drawings

HAIR ANALYSIS METHOD

CROSS REFERENCE TO RELATED APPLICATIONS

This is a division of application Ser. No. 08/813,376, filed Mar. 6, 1997, now U.S. Pat. No. 6,022,693, which is a continuation-in-part of U.S. application Ser. No. 07/737,703 filed on Jul. 30, 1991, now co-pending which in turn is a continuation-in-part of U.S. application Ser. No. 07/285,123 filed Dec. 16, 1988, now U.S. Pat. No. 5,324,642, which in turn is a continuation-in-part of U.S. application Ser. No. 07/215,591 filed Jul. 6, 1988, now abandoned, which in turn is a continuation-in-part of U.S. application Ser. No. 07/138,515, filed December 28, 1987, now abandoned.

FIELD OF THE INVENTION

This invention relates to an improved analytical method which effectuates the relatively rapid solubilization of hair and direct analysis of organic analytes, e.g., drugs of abuse, present in hair and other keratinized structures, e.g., fingernails and toenails, without effecting the structure of the analyte or being detrimental to biological analyte probes, e.g., antibody, RNA/DNA and bio-receptor probes. The analyte can be analyzed by adding the analyte probe directly to the solubilized keratin structure containing the analyte to determine the identity of the analyte as well as the extent and duration of its consumption by a subject.

BACKGROUND OF THE INVENTION

In the past, hair analysis techniques for the detection of trace metals were developed that purported to provide information on an individual's nutritional status. One objection to the use of these techniques is the difficulty of distinguishing between trace metals deposited in hair from the bloodstream and metals which have become embedded in hair through external contact with, for example, water and cosmetic agents. Consequently, these techniques are not considered useful by the medical community for diagnosing nutritional problems, and therefore have not been considered sufficiently accurate to determine the level of a particular trace metal consumed by a subject.

The problems with previous hair analysis techniques have caused reliance on urine and blood analysis techniques for the detection of ingested chemicals, e.g., drugs-of-abuse, medications and toxic chemicals, in a subject. However, these techniques also are known to be disadvantageous in that the duration and intensity of use or exposure cannot be ascertained. Urine and blood analysis, at best, can provide short term information concerning ingested drugs or chemicals such as drugs-of-abuse. In addition, there are also problems with the interpretation of such results. For example, the detection of a low level of ingested chemical in the urine could mean that a subject ingested a small amount of the drug or chemical very recently or a larger amount several days earlier. Thus, chronic drug use cannot be determined with these methods without repeated testing.

In response to the problems of establishing a reliable and accurate method that would measure both the duration and intensity of use of drugs-of-abuse, medications, toxic chemicals, etc., work performed by Dr. Werner A. Baumgartner, as reported in "Radioimmunoassay of Hair for Determining Opiate Abuse Histories", J. Nucl Med 20:749–752 (1979), determined that long-term histories of exposure to drugs-of-abuse can be obtained through the analysis of mammalian body hair, since these substances are "trapped" within individual hair fibers during their synthesis. In this respect, hair was shown to act like a tape recorder, i.e., past exposure histories can be evaluated through sectional analysis of hair samples. It was found that heroin, once in the bloodstream, will find its way into hair as it is synthesized.

Thus, it was discovered in this study and confirmed by subsequent studies that a variety of chemicals, such as drugs-of-abuse, medications, toxic chemicals, etc., hereinafter collectively referred to as "analyte", are trapped by hair during its synthesis and that these substances are "locked up" in hair for essentially the duration of the hair. This was found to be true for head and body hair as well as for other keratinized structures such as fingernails. Suzuki et al., Forensic Sci. International, 24:9–16, 1984. These entrapped substances cannot be washed out of hair, and are completely released only upon the complete, or nearly complete, destruction of the hair fiber.

Prior art methods of extracting an analyte from hair included subjecting the hair to hot methanol solutions (Baumgartner et al., J. Nucl Med 20, 748, 1979) and by overnight incubation of hair in an alkaline or acid medium. D. Valente, et al., Clinical Chemistry, 1952, Vol. 27, No. 11, 1981. Prior methods also include the use of a mortar and pestle to release the entrapped analyte in conjunction with a solvent.

However, solvent extraction procedures suffer from several problems in accurately determining the presence and amount of an ingested analyte. One of these problems is that the solvent extraction methods frequently remove only a small unknown and variable fraction of the total analyte present in the hair sample. Such methods also tend to be time consuming, and generally involve elevated temperatures which may damage the analyte. Another disadvantage is that different analytes require different solvents for extraction. For example, a hair sample containing morphine, phencyclidine ("PCP"), cocaine and marijuana has to be extracted sequentially with several different solvents, which is a very time consuming procedure, particularly since the frequently toxic solvents have to be evaporated in expensive fume hoods before analysis can proceed.

Other methods and studies pertaining to the degradation of hair and hair analysis include:

O. Suzuki, et. al., in a publication by Elsevier Scientific Publishers Ireland Ltd., discloses a method for detecting methamphetamine and amphetamine in nail clippings or hair in which the substance was first washed in a mixture of methanol and water and dissolved in sodium hydroxide, followed by analysis of the extracted drug.

A. W. Holmes, in Textile Research Journal, 706–712, August 1964, discloses the degradation of human hair by papain using sodium sulfite as enzyme activator.

Annette M. Baumgartner, et al., in the Journal of Nuclear Medicine, 20:748–752, 1979, discloses the extraction of morphine and heroin from hair by pulverizing hair with a mortar and pestle followed by treatment with methanol.

D. Valente, et al., in Clinical Chemistry, Vol. 27, No. 11, 1981, discloses Dr. Baumgartner's technique of subjecting hair to a treatment of hot methanol to effectuate extraction of drugs of abuse as well as the author's technique of extracting morphine in an acid or alkaline medium.

A. M. Baumgartner, et al., in Journal of Forensic Sciences, p. 576–81, July 1981, discloses the extraction of PCP with mortar and pestle followed by treatment with methanol. The extracted PCP was then analyzed with RIA.

Smith et al., in Journal of Forensic Sciences, Vol. 26, No. 3, July 1981, pp. 582–586, disclose the testing of hair for the presence of phenobarbital, in which a single head hair was washed, dried, cut in 2 mm lengths and added to 0.2 ml 0.1% SDS/saline solution, and a sample assayed by radioimmunoassay.

W. A. Baumgartner, Black. et al., in J. Nucl Med 23: 790–892, 1982, discloses the extraction of cocaine from hair samples by refluxing the hair samples in ethanol followed by RIA analysis.

Ishiyama, et al., in Journal of Forensic Sciences, Vol. 28, No. 2, April 1983, pp. 380–385, disclose a method whereby hair from methamphetamine addicts was dissolved using 1.5 N hydrochloric acid at a pH between 1 and 2, followed by analysis using a gas chromatograph and mass spectrometry.

K. Puschel, et al., in Forensic Science International, 21 (1983) 181–186, discloses the dissolving of hair samples by exposure to sodium hydroxide and heat followed by analysis for the presence of morphine by RIA.

O. Suzuki, et al., in Journal of Forensic Sciences, Vol. 29, No. 2, April 1984, pp. 611–617, discloses the detection of methamphetamine and amphetamine in a single human hair by gas chromatography and chemical ionization mass spectrometry. The hair sample was first dissolved in a sodium hydroxide solution to which was added N-methylbenzylamine.

N. J. Haley et al., in Clin. Chem. 31/10, 1598–1600 (1985), discloses the analysis of hair for nicotine and cotinine, in which washed hair samples were dissolved in a buffer solution containing gelatin, sodium chloride, Tris and EDTA, and adjusted to pH 7.4. Samples were then analyzed by radioimmunoassay.

Sramek, Baumgartner, et al., in A.M.J. Psychiatry 142:8, August 1985, discloses the analysis of hair samples of psychiatric patients with methanol extraction and radioimmunoassay.

Baumgartner, et al., in Clinical Nuclear Medicine, Vol. 10, 4, September 1985, discloses the benefits of extracting entrapped drugs of abuse from hair followed by RIA analysis.

Gill, et al., in Nature, Vol. 318, p. 577 (1985) discloses the use of an SDS/proteinase k/dithiothreital mixture to extract DNA from whole blood, whole semen, vaginal fluid, hair roots, bloodstains and semen stains. The article states that "no DNA could be isolated from hair shafts".

Smith et al., in J. Forensic Sci. 1986, 31(4), 1269–73, discloses the detection of cocaine in perspiration, menstrual blood stains and hair using RIA.

M. Margio, et al., in "Determination of Morphine and Other Opioids in the Hair of Heroin Addicts by HPLC and MS/MS" at the International Conference, University of Verona, Jun. 25–26, 1986, discloses various methods to assay morphine from hair samples.

M. Marigo, et al., in the Journal of Analytical Toxicology, Vol. 10, July/August 1986, discloses a method for the quantitative determination of morphine contained in the hair of heroin addicts, by means of heat-acid hydrolysis, pre-column dansyl derivatization, straight phase liquid chromatography and fluorescence detection.

Smith, et al., in Journal of Forensic Sciences, Vol. 31, No. 4, October 1986, pp. 1269–1273, disclose a method for the analysis of hair for the presence of drugs whereby hair samples were first washed, cut into small segments, mechanically pulverized for six minutes, refluxed in ethanol and the samples analyzed using radioimmunoassay.

M. Michalodinitrakis, Med.Sci.Law (1987), Vol. 27, No. 1, discloses the detection of cocaine in rats from the analysis of hair samples, which were dissolved upon exposure to 1.5 N HCl, which brought the pH value to 1–2, following incubation with 0.01 N Hcl at 37° C. for one hour.

Pelli, et al., in Biomedical and Environmental Mass Spectrometry, Vol. 14, 63–68 (1987) discloses a procedure for the identification of morphine in the hair of heroin addicts in which hair is treated with diethylether and hydrochloric acid followed by dissolution of the dried extract in methanol.

Higuchi et al., in Nature, Vol. 332, p. 543 (1988) disclose a method for dissolving hair at pH 8 by the action of dithiothreitol, proteinase K, and 2% sodium dodecylsulfate in order to extract DNA from the digest by a complex chemical extraction method.

Also noted are certain patents, e.g., U.S. Pat. Nos. 3,986, 926, 3,966,551, 3,939,040 and 3,623,950, which pertain to depilatory agents for the tanning of hides, and disclose the use of certain enzymes, including papain, in the dehairing process.

However, these and other prior art methods have proven disadvantageous for the reasons noted above and/or because they degrade the analyte probes (e.g., antibodies) of biological analytical methods, thereby preventing the use of such highly sensitive analytical techniques.

Thus, there exists a need for an analyte detection method that can rapidly and completely solubilize a certain analyte from keratinized structures of the body such as hair, fingernails and toenails of a subject and which permits direct analysis of the identity of the analyte and the duration of use of the analyte in, or exposure to, a subject, without destroying the analyte of interest and/or an analyte probe of biological analytical methods.

SUMMARY OF THE INVENTION

It is an object of the invention to provide a drug and chemical detection method.

It is another object of the invention to provide a drug and chemical hair analysis method.

It is another object of the invention to provide a reliable method of digesting head and body hair and other keratinized structures of the body and directly analyzing the identity and amount of analyte contained therein, and, where applicable, of determining the duration and extent of exposure of the analyte in a subject.

It is yet another object of the invention to provide a hair analysis method that solubilizes an analyte from the inner core of hair without causing damage to the analyte.

It is yet another object of the invention to provide a reliable hair digestion and direct analyte detection method that effectively permits the use of highly accurate biological analytical methods such as radioimmunoassay.

It is yet another object of the invention to provide a reliable hair analysis method that may be performed in a lesser period of time than known hair analysis methods.

It is yet another object of the invention to provide a drug detection method effective for use in the drug testing industry standard five-drug screen for marijuana, cocaine, opiates, methamphetamine and phencyclidine.

These and other objects are achieved by the novel analysis method according to the invention, which comprises preparing a mixture containing dithiothreitol (DTT) or dithioerythritol (DTE), an enzyme suitable for the digestion of keratinized structures and a sample of a keratinized structure; permitting DTT or DTE to activate the keratinized structure and/or the enzyme; permitting the enzyme to at least substantially digest the sample of keratinized structure to form a keratin digest solution; deactivating the DTT or DTE; and subjecting a portion of the keratin digest solution to analysis to detect the identity and amount of the analyte, if present, in the keratinized structure sample.

The preferred keratinized structure is hair. The enzyme may be any enzyme that, together with DTT or DTE, digests hair, and preferably is a protease including papain, chymopapain, or proteinase K. In order to accelerate the process, metal ions preferably in the form of metal salts may be added to the digest solution to deactivate any remaining DTT or DTE in the mixture which, if left active, would cleave the disulfide bond of the antibody of a biological analytical method such as an immunoassay, e.g. radioimmunoassay.

DETAILED DESCRIPTION OF THE INVENTION

In accordance with the present invention, a method is provided that permits the rapid and complete digestion of head or body hair or other keratinized structure of an individual who may previously have ingested one or more analytes, followed by the identification of the analyte by known analytical biological probes such as the rapid and highly sensitive immunoassays. The release of the analyte into a digest solution from the interior of hair is effectuated according to the invention without damaging the analyte trapped within the organic matrix of the hair fiber which is to be analyzed, and without harmful effect on a subsequently-used probe (e.g., antibody) of a biological analytical method. The invention also permits the detection of past use patterns in a subject over extended periods of time without performing repeated testing as is necessary in conventional testing methods which measure the content of the analyte in samples of blood or urine. It has been found that the amount of analyte entrapped in hair of the same individual is directly proportional to the amount of analyte ingested.

A sample of a keratinized structure, e.g., hair, is first collected from a subject who may have ingested a particular analyte. Preferably, the hair sample is first washed by known methods to remove analyte or other drug or chemical which may have been deposited on the surface of the hair by external contact rather than by actual consumption. The hair sample is then subjected to treatment with a particular enzyme, together with a particular enzyme/substrate activator, so as to effectuate the complete or nearly complete digestion of the organic matrix of the hair fiber, known as keratin. The subject analyte that has been "entrapped" within the organic matrix of the hair is then released into solution, or even if protein bound, the analyte is accessible to the antibody employed in protein-based analytical methods. In order to fully and accurately carry out the method according to the invention, a complete digestion of the sample is desirable.

Any enzyme that acts quickly to digest hair in conjunction with DTT or DTE without having a detrimental effect on the analyte is useful in the invention. In this regard, proteases are preferred for use in the invention. Most active, and therefore most preferred for use in the invention, are the proteases papain, chymopapain and proteinase K.

A number of other proteases have been found to be effective in the method according to the invention at low pH values (e.g., pH 7–9), namely, protease Type IV (bacterial, from *Streptomyces caespitosus*), Type VIII (from *Bacillus subtilis*), Type XI (proteinase K, fungal, from *Tritirachium album*), Type XIV (pronase, from *Streptomyces griseus*), Type XVI (from *Bacillus subtilis*), Type XVIII (Newlase, from Rhizopus species), Type XIX (from *Aspergillus sojae*), Type XXI (from *Streptomyces griseus*), Type XXIV (bacterial), Type XXVII (Nagarase), Type III (Prolase) and Type XXIII (from Aspergillus Oryzae) (all available from Sigma Chemical Co., St. Louis, Mo.).

As noted above, certain art-recognized procedures provide for the use of papain for use as a hair depilatory. These depilatory methods remove hair from hides and skin by softening it sufficiently so as to permit its ready removal by scraping or other mechanical means, and utilize inexpensive and less effective sulfhydryl enzyme and substrate activators such as thioglycolic acid or cysteine. These methods only partly degrade the hair and do not provide for the complete chemical digestion of the hair. A mere softening of the hair does not lead to the complete, or nearly complete, digestion of hair which is necessary in order to obtain a complete release of "entrapped" analyte. Moreover, the sulfhydryl enzyme activators used in these depilatory methods are also harmful to certain biological analyte probes such as antibodies.

In contrast to these depilatory methods, the method of the present invention utilizes "DTT" (2,3 dihydroxybutane-1,4-dithiol) or its isomer "DTE" (2,3 dihydroxybutane-1,4-dithiol) as the substrate and enzyme activating agent. Surprisingly, it has been found that the use of DTT or DTE in the process of the invention significantly enhances the digestion of the sample within a relatively short period of time, e.g., about three hours, resulting in the release of the analyte into the digest solution. Particularly surprising is that the invention may be used in the industry standard five-drug screen, in that it does not negatively impact upon any of those five drugs or their corresponding antibodies in the analysis step of the invention.

This high activity of the enzyme is believed to be due, at least in part, to the activation of the keratinized structure substrate itself by DTT and DTE, presumably by the action of DTT and DTE in opening up disulfide bonds in the keratinized structure, which facilitates enzymatic attack.

Once the protein of the keratinized structure has been completely or at least substantially digested, thereby releasing the analyte into the solution mixture, it has been found to be necessary to deactivate DTT/DTE and the sulfhydryl enzymes prior to subjecting the analyte to biological analytical probes, since the sulf-hydryl enzymes and enzyme/substrate activator(s) may interfere with the structural integrity of protein components of such methods.

The task of deactivating the sulfhydryl-dependent enzymes such as papain has proven difficult since after the digestion step, the enzymes are "buried" in a "sea" of sulfhydryl groups belonging to the released hair proteins and enzyme/substrate activating agents. Known sulfhydryl blocking agents are ineffective in deactivating the enzymes, since the known sulfhydryl blockers tend to bind to the degraded hair proteins and DTT or DTE and not necessarily to the enzyme sulfhydryl sites critical for blocking the activity of the enzymes. Thus, it is not possible to effectively utilize the protein-based analytical methods if the enzyme sulfhydryl sites are still active.

It was quite surprising, therefore, that DTT and DTE act not only to activate enzymes and/or the keratinized structure substrate causing unexpectedly high hair digestion activity, but that they also may act to deactivate the enzyme by a direct or indirect (enzyme self-deactivation) mechanism after the enzyme effectuates the complete, or nearly complete, digestion of the hair protein. Typically, the enzyme deactivation occurs within about four to five hours after exposure of the DTT or DTE to the enzyme, which is a sufficient amount of time for the enzyme to effectuate the digestion of the hair sample. Once the enzyme has been deactivated, it has been found that the enzyme cannot be reactivated or regenerated by exposure to fresh DTT or DTE.

Deactivation of at least certain of the non-sulfhydryl dependent proteases, e.g., proteinase K, by its inhibitor, phenylmethyl sulfonyl chloride, is generally not required since the enzyme has not been found to be active against the antibodies used in protein based immunoassay techniques.

It also has been found that active DTT or DTE present in the hair digest solution constitutes a hazard to the structure and activity of other proteins to which it is exposed, e.g., antibodies utilized in radioimmunoassay. Thus, it was a further surprising result that DTT or DTE in the reaction mixture may not only act to deactivate the enzyme, but itself deactivates in the digest solution without the introduction of an inhibitor. Typically, DTT and DTE will deactivate after the hair sample has been digested, less than about 14 hours after its first exposure to the enzyme depending on the various concentrations and amounts of the enzyme and DTT or DTE utilized, the pH, temperature, amount of hair sample, etc.

Thus, in accordance with the method of the invention, complete digestion can be carried out in a relatively short period of time, e.g., overnight, and the digest solution, which includes the released analyte of interest, can be directly subjected, effectively and accurately, to protein-based ligand assay analysis methods the next morning. Typically, the entire method, from the washing of hair samples to the identification of the analyte, should take no longer than about 16–20 hours. Little or no intervention by the individual performing the method is needed to release the analyte from the hair sample once the enzyme and DTT or DTE come into contact with the hair sample.

Alternatively, it has been discovered that the addition of certain metal ions, typically in the form of metal salts, to the digest solution results in a rapid deactivation of DTT or DTE. The addition of low amounts of such metal salts to the digest solution after digestion of the sample significantly accelerates the time in which the hair digest mixture can be subjected to the immunoassay method since it is not necessary to wait for DTT or DTE to deactivate on its own. This discovery is particularly surprising as not all metal ions are effective in deactivating DTT and DTE, or otherwise are not useful in the invention.

Most effective for use in the invention are certain metal salts which surprisingly do not precipitate out of the solution after chemically linking with, and deactivating, DTT/DTE. It is important that precipitation not occur in the digest solution because such precipitation could result in a loss of analyte by adsorption. Preferably, precipitation is prevented by maintaining the pH of the digest solution at about 6–8, and most preferably at about 7. One way this may be accomplished is by the addition of one molar Trizma base. Surprisingly, the most preferable pH of about 7 is also the optimum pH for the performance of radioimmunoassay ("RIA").

In addition to $Cu^{++}$ salts (e.g., copper sulfate) as described in Applicant's U.S. Pat. Nos. 5,466,579 and 5,324,642, salts of $Zn^{++}$ (e.g., zinc sulfate and zinc nitrate); $Mn^{++}$ (e.g., manganese sulfate); $Fe^{++}$ (e.g., ferric sulfate and ferric chloride); and $Fe^{+++}$ (e.g., ferrous sulfate) are particularly effective and preferred for use in the invention. Also effective for use in the invention are salts of $Pb^{++}$ (e.g., lead acetate and lead nitrate); $Cd^{++}$ (e.g., cadmium chloride); $Hg^{++}$ (e.g., mercuric chloride); $Ag^{++}$ (e.g., silver nitrate); and $Co^{++}$ (e.g., cobalt chloride).

Typically, about 100 microliters of metal salt (10 mg/ml) is added to 1 ml of hair digest solution about 4 to 5 hours after contacting the enzyme and DTT (or DTE) with the hair sample so as to permit the enzyme and DTT (or DTE) sufficient time to digest the hair sample.

Similarly, any salt of arsenite, and preferably sodium arsenite ($NaAsO_2$), may be utilized in the invention to remove residual DTT or DTE by formation of a precipitable compound. Typically, 100 microliters of a 100 mg/ml solution of sodium arsenite is added to 1 ml of hair digest solution to effectuate the deactivation of DTT and DTE. However, arsenite is not preferred because a precipitate usually develops. It may, however, be useful in certain circumstances.

Once the rapid and effective digestion of the sample occurs, the digest solution may then be subjected to direct analysis by art recognized protein-based analytical methods such as RIA. Such methods are preferred for use in the invention because RIA and related immuno- or ligand assays are currently the only known mass production procedures having the required sensitivity and convenience for measuring the low concentrations of analytes contained in hair samples. The use of these methods is preferred because only about 0.5 to 1.0 mg. of hair is necessary for analysis by RIA and other protein-based analytical methods.

Other analytical methods may be utilized in place of or in addition to the protein-based analytical methods, including instrumental means such as chromatography, mass spectrometry, etc. In particular, these methods may be used to confirm positive results obtained in RIA. Because these methods are not protein-based, the steps of deactivation of the enzyme and DTT or DTE is not necessary when using non-protein-based analytical techniques. However, the speed and gentleness of the extraction method according to the invention and the ability to quantitate the extraction efficiency through the inclusion of a "spike", i.e., the inclusion of a known amount of deuterated analyte, makes the presently disclosed digestion method also the method of choice for instrumental analysis methods such as gas chromatography and mass spectrometry.

The method according to the invention has been found to be effective in detecting the use and prior use of drugs of abuse such as cocaine, morphine/heroin, marijuana, phencyclidine or "PCP", methaqualone and methamphetamine. Moreover, the method according to the invention has been found to be effective in determining prior usage of prescription drugs such as digoxin, methadone and benzodiazepines. It is contemplated that any organic analyte present in the bloodstream of an individual which is transferred to the hair during its synthesis can be extracted and analyzed in accordance with the method of the invention.

In carrying out the method, it is preferred that an aqueous solution of about 110 mg DTT or DTE/10 ml water be used, although concentrations of DTT or DTE of about 50–200 mg/10 ml water are effective in the method. It is preferred that the weight ratio of DTT or DTE to papain or chymopapain be about 110:2 [when enzyme purity is 16–40 BAEE units/mg protein], although efficacious results have been observed at weight ratios of DTT or DTE to papain or chymopapain ranging between about 110:1 to about 110:4. With respect to proteinase K and other proteases, it is preferred that the weight ratio of DTT or DTE to proteinase K (or other proteases) be about 1200:1 (when enzyme purity is 10–20 units per mg. protein), although weight ratios of 1200:0.5 to about 1200:2 also will be effective.

The concentration of hair protein is preferably kept constant at about 10 mg hair/cc of digest solution so as to prevent variable matrix effects in a subsequently utilized protein-based analytical method.

The enzymatic digestion of hair and other keratinized structures, according to the method of the invention, may be conducted at low temperatures and near neutral pH. When papain, chymopapain or other sulfhydryl dependent enzyme is utilized as the enzyme, the method may be performed at a temperature of between about 20° C. and 40° C., and at a pH between about pH 8.8 and 10.5. Preferably, the pH of the method is between about 8.8 and 9.5 at a temperature of about 37° C.

When proteinase K or other proteases are utilized as the enzyme, it is preferable to perform the method between about 20 and 40 degrees centigrade and at a pH between about 7 and 9. When the temperature is about 37 degrees centigrade and the pH about 7.0 or below, the risk of altering the structure of a particular analyte is at a minimum. Other enzymes which digest hair under neutral or acid conditions include: Protease Type XIV (Pronase), Type III (Prolase), Type IV, Type VIII, Type XVI, Type XVIII, Type XIX, Type XXIV, Type XXVII (Nagarse), Type XXVIII, Type XXI and Type XXIII.

Under certain circumstances, it is advantageous to perform the method according to the invention at a lower than usual pH in order to preserve the chemical structure of the analyte. As stated above, the digestion typically will occur at a pH between about 8.8 and 10.5 when a sulfhydryl dependent enzyme (e.g., papain) is utilized and between 7 and 9 when a protease such as Proteinase K is utilized. At any pH in either of these ranges, however, certain analytes may become unstable or hydrolyze to a different form, which may impact on the measure of both quantity and quality of the analyte in the subsequent analysis step.

Thus, for example, at a pH of about 7, the heroin metabolite, 6-monoacetylmorphine, breaks down rapidly to morphine, thereby making heroin users indistinguishable from morphine users. In addition, the stability of cocaine is also quite pH dependent, and the performance of the method at an improper pH may lead to a false interpretation of a positive cocaine result.

Ingested cocaine naturally hydrolyzes to benzoylecgonine in the blood and eventually ends up entrapped in hair both as cocaine and benzoylecgonine. The digestion of hair from a cocaine user will lead to the release of both cocaine and benzoylecgonine from the hair into solution thereby resulting in the conclusion that a positive cocaine hair analysis result was caused by cocaine ingestion.

In situations where an individual has not ingested cocaine but is only exposed to cocaine environmentally, contaminated hair will contain only cocaine and not the benzoylecgonine metabolite. Thus, the absence of benzoylecgonine confirms lack of drug use. Conversely, the presence of benzoylecgonine refutes any claim that a positive result was caused by the external contamination of a hair sample, i.e., by faulty, ineffective washing of the sample by the laboratory to remove cocaine contaminants deposited from the environment. However, cocaine tends to hydrolyze to benzoylecgonine at a pH above about 6.5 and a temperature of 37° C. As a result, the certainty of distinguishing between drug use and external contamination can only be achieved if the pH of the digest solution is maintained so as to avoid the production of significant quantities of benzoylecgonine.

Thus, in the case of certain analytes such as cocaine which may be chemically altered by a higher pH, it is desirable to perform the method of the invention at a pH which avoids hydrolysis or other chemical reaction of externally deposited analyte which inadvertently has ended up in the digest solution. In the case of cocaine, performance of the method at a pH below about 6.6 at 37° C. will ensure that the benzoylecgonine in the sample is directly related to ingested cocaine and not to externally deposited cocaine.

According to the invention it has been found that certain biological detergent compounds useful for solubilizing biological membrane components aid in the digestion of hair at a relatively low pH while not interfering with enzymatic activity or the antibody-antigen reaction which will influence the sensitivity of the immunoassay. This is surprising and unexpected since other biological detergents have been found to be unsuitable for use in the invention because they are ineffective in aiding digestion at the desired low pH, they deactivate proteinase K or other hair protein digestion enzymes and/or they impact on the binding of the analyte by the antibody thereby drastically reducing the sensitivity of the immunoassay. See, e.g., Higuchi, R. et al., "DNA Typing From Single Hairs", *Nature,* 332:543–546, 1988.

These biological detergents, together with an appropriate enzyme (e.g., protease and sulfhydryl enzymes) and activator (e.g., DTT and DTE), are effective in aiding the digestion of the hair sample at a lowered pH in the range of about 5.8 and 8. Those detergents found to be useful in the invention include the bile acid detergents, such as glycocholic acid, cholic acid, taurocholic acid, deoxycholic acid, glycodeoxycholic acid, taurodeoxycholic acid and salts thereof, including sodium salts. Other detergents effective for use in the invention are sulfo-betaines, such as the Zwittergents®, and betaines, such as Empigen BB (N-dodecyl-N,N dimethylglycine) (all available from Calbiochem Corp., La Jolla, Calif.).

Still other detergents which are useful in aiding the digestion of hair according to the invention at a relatively lower pH are the alkylglucosides, including hexyl-β-D-glucopyranoside, heptyl-β-D-glucopyranoside, octyl-β-D-glucopyranoside, nonyl-β-D-glucopyranoside, decyl-β-D-glucopyranoside, dodecyl-β-D-maltoside and octyl-β-D-thioglucopyranoside (OSGP). Mixtures of alkylglucosides, such as the product ELUGENT (Calbiochem), are also effective.

Particularly preferred for use in the invention are the bile acids cholic acid and glycocholic acid which aid in the digestion of hair at a pH in the range of about 6.3–8. The deoxycholates such as deoxycholic acid and glycodeoxycholic acid are effective in aiding in the digestion of hair at a pH above about 7.

As discussed above, the hydrolysis of cocaine occurs at a pH of about 6.6 and above at 37° C. Thus, to avoid significant hydrolysis of cocaine to benzoylecgonine, the digestion preferably is performed at a pH of 6.5 or below, and typically in the range of about 6.3–6.5.

Surprisingly, certain of these detergents are efficacious when the industry standard five-drug screen for the most common drugs of abuse in the United States, i.e., marijuana, cocaine, phencyclidine, methamphetamine and opiates, is performed using the method of the invention. Thus, they do not impact on any of the analytes or antibodies involved in the five-drug screen, and do not result in false negatives or positives. This is particularly surprising given the fact that the chemical nature of these five analytes ranges from highly lipidic drugs such as PCP and marijuana to highly water soluble drugs such as benzoylecgonine and morphine.

The particular detergents most effective for use in the five-drug screen are cholate, deoxycholate, cholic acid, deoxycholic acid, octyl-β-D-glucopyranoside and octyl-β-D-thioglucopyranoside. The bile acid detergents, alkylglucosides, sulfobetaines and betaines are most preferred when a screen is performed that includes cocaine, opiates, phencyclidine and methamphetamine. In a screen solely for cocaine, the preferred detergents are cholic acid, Zwittergents®, alkylglucoides, and N-dodecyl-N,N dimethylglycine.

Of the sulfo-betaine detergents manufactured by Calbiochem Corp. of La Jolla, Calif., Zwittergent® SB3-14 (CAS Registry No. 14933-09-6, N-tetradecylsulfobetaine or 3-(dodecyldimethylammonio) propane-1-sulfonate.) is preferred. Digestion of hair using the Zwittergent® sulfobetaine detergents typically occurs at about pH 6.3 at 37° C. Zwittergents® are of the class of detergents known as sulfo-betaines having the general structure:

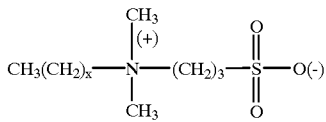

wherein x may be any number which provides an effective biological detergent. Preferred are those compounds wherein x is in the range of 7–16. Most preferred is the detergent when x is 14. Other Zwittergent® sulfo-betaine detergents useful in the invention include:
1. Zwittergent® SB3-08 wherein x=7 [N-octyl sulfo betaine or 3-(Octyldimethylammonio) propane -1-sulfonate] [CAS # 15178-76-43].
2. Zwittergent® SB3-10 wherein x=9 [N-D-dodecylsulfobetaine or 3-(dodecyldimethylammonio) propane-1-sulfonate] [CAS Registry # 15163-36-7].
3. Zwittergent® SB3-12 wherein x=11 [N-dodecylsulfobetaine or 3-(Dodecyldimethylammonio) propane-1- sulfonate] [CAS #14933-09-6].
4. Zwittergent® SB3-14 wherein x=13 [N-tetradecylsulfobetaine or 3-(Dodecyldimethylammonio) propane-1-sulfonate] [CAS # 14933-09-6].
5. Zwittergent® SB3-16 wherein x=15 [N-Hexadecylsulfobetaine or 3-(Hexadecyldimethylammonio) propane-1-sulfonate] [CAS #2281-11-0]

The bile acid detergents and Calbiochem Zwittergents® SB3-8, SB-10, SB3-12, SB3-14 and SB3-16 (x in the range of 7–16) are preferred in effectuating the digestion of hair at a relatively lower pH which is desirable in methamphetamine, PCP and opiates assays. The cholate and Calbiochem Zwittergents® are preferred for use in the cocaine assay. The cholate and deoxycholate detergents are preferred for use in marijuana screening assays.

In practice, the biological detergent is mixed with the aqueous digest solution of the activator such as DTT (or DTE) and the enzyme (preferably proteinase K) prior to contact of the solution with the hair sample at a preferred temperature range of about 30–40° C. as described herein. Typically, about 1–2 mg of biological detergent is added to about 1 cc of digest solution.

In another embodiment according to the invention, an ion exchange resin is employed to remove from the hair digest solution a substance which uniquely interferes with the marijuana assay. This interference has occurred with all currently available commercial RIA kits suitable for detecting cannabinoids. The interfering substance, effectively present in every hair sample in varying amounts from individual to individual and believed to be naturally occurring in hair, appears to interfere with the assay as a result of a cross reaction with the marijuana RIA antibody (i.e., specific to cannabinoids) rather than by matrix effects. This appears to be the case because dilution of the interfering substance produces an asymptotic curve which appears identical in shape to the calibration curve obtained. with the carboxytetrahydro-cannabinol ("carboxy-THC") standard used for an RIA marijuana assay, rather than producing an S-shaped dilution curve which would have been expected if matrix effects were the cause of the interference. It appears that this interfering substance is lipidic and bears a close resemblance in structure at the immunological binding site to carboxy-THC.

Because of its similarity to carboxy-THC, and other cannabinoids such as tetrahydrocannabinol ("THC"), the interfering substance results in false positive results in assays on hair digests using RIA to determine marijuana exposure. In other words, the RIA erroneously will identify the interfering substance as a cannabinoid from exposure to marijuana, even in individuals not exposed to marijuana. Thus, it is necessary when performing an RIA assay for marijuana exposure to somehow remove the interfering substance from the digest solution prior to subjecting the solution to immunoassay analysis.

Since the presence of this interfering substance in hair is a new discovery, there is no method known to the art for removing it. Removal of the interfering substance from the digest solution is further complicated by its similarity to lipidic carboxy-THC and THC, the more common diagnostic analytes in a marijuana assay. Many filtering techniques with the capability of filtering out undesirable substances are not effective in removing the interfering substance from the digest solution, because they either do not effectively remove the interfering substance, and/or because they remove the analytes, e.g., THC and Carboxy-THC.

It was thus surprising that there exists in hair an analyte indicative of marijuana exposure which does not possess many of the same lipidic properties of the interfering cross reacting substance but yet will react with the cannabinoid antibody used in the RIA assay for marijuana. The exact chemical structure of this immunoreactive substance(s), or modified-lipidic marijuana analyte, is unknown. However, its presence in the hair sample will indicate marijuana use.

Also surprising is the discovery that the interfering substance may be removed from the digest solution without removing the newly discovered modified-lipidic marijuana analyte by the use of certain commercially available ion exchange resins. It has been found that suspensions of certain ion exchange resins upon contact with the digest solution will remove the interfering substance along with certain cannabinoids such as THC from the digest solution, but will leave in the digest solution other diagnostic cannabinoids, such as the modified lipidic marijuana analyte, which then may be detected by commercially available RIA kits utilizing a cannabinoid antibody. The use of these ion exchange resins to remove the interfering substance, thus permitting the detection of the modified-lipidic marijuana analytes in the RIA assay without interference, is both convenient and cost effective.

Effective ion exchange resins are both anionic and cationic. They generally are commercially available, such as from Sigma Chemical Co. of St. Louis, Mo. However, they have been found to be most effective not in the form in which they are commercially available (generally course, fast settling particles), or in the way they are generally used (e.g., packed columns) but when contacted with the digest solution in the form of a suspension, e.g., when broken apart into much smaller, slowly settling particles by vigorous stirring and made into a fine suspension of these small particles. Effective ion exchange resins include:

1. Anion exchangers on dextrose such as DEAE Sephadex® (A-25 and A-50 Diethylaminoethyl Sephadex®) and QAE Sephadex® (Q-50 Diethyl-[2-hydroxypropyl] aminoethyl Sephadex®);
2. Anion exchangers on agarose such as DEAE Sepharose® CL-6B (Diethylaminoethyl Sepharose®) and Q Sepharose®;
3. Anion exchangers on cellulose such as DEAE-Sephacel® (Diethylaminoethyl Sephacel®); Ecteola Cellulose (Epichlorohydrin Triethanolamine Cellulose); PEI Cellulose (Polyethyleneimine Cellulose); QAE Cellulose (Diethyl-[2-Hydroxypropyl]aminoethyl Cellulose); and DEAE cellulose;
4. Cation exchangers on dextran, such as SP Sephadex® C25 (Sulfopropyl Sephadex®)
5. Strongly acidic cation exchangers on polystyrene, such as Amberlite® 200 (active group: sulfonic acid, sodium form); Dowex® HCR-S (active group: nuclear sulfonic acid, hydrogen form) and Dowex® macroporous resin (active group: nuclear sulfonic acid, hydrogen form).
6. Specialty Exchangers such as benzyl DEAE cellulose (Benzyl Diethylaminoethyl cellulose) and TEAE cellulose (triethylaminocellulose).

The concentration of the resin will vary depending on the resin employed. Concentrations may vary up to about 50% (wt./vol.). For example,.a suspension of DEAE Sephadex® A25 in deionized water preferably is prepared using about 3 to 9 gm. resin/100 ml water. The suspension is allowed to swell. At least one hour of swelling at room temperature has been found to be adequate. After swelling, the suspension is stirred or shaken vigorously for at least thirty minutes and preferably up to about sixty minutes until a very fine suspension is obtained.

Preferably, the suspension has a settling time in the range of 50–60 minutes compared to about 10–15 minutes of an aqueous suspension of an unshaken resin. Vigorous stirring or any other method which results in the break up of the resin into small particles provides the optimum results in removing the interfering substance from the digest solution.

To achieve removal of the interfering substance, approximately equal parts of hair digest solution and fine suspension are mixed together. The ratio of suspension to hair digest solution, however, will vary depending on the resin used and its concentration in the resin suspension. Generally, the ratio of digest solution to suspension is 4 to 3, if a suspension of 3 to 9% (wt./vol.) is used. The mixture is rotated so that the suspension and digest solution are in direct contact. Distilled water is then added, the mixture centrifuged and a sample of the supernatant from the resinated digest solution assayed according to the invention.

While the method according to the invention for removing the interfering substance has been described in connection with a digest solution, it is recognized that the ion exchange resin suspension may be used in any hair analysis method where removal of the interfering substance is desirable or necessary, provided that the analytes are ultimately contained in an aqueous albumin solution near neutral pH as required for the RIA assay. The resin suspensions may be used, for example, together with known hair extraction (acid, base or solvent) methods or any other method which disrupts a hair sample and results in the release into a solution at least a portion of the contents of a hair sample which includes the interfering substance.

In contrast to other available analyte detection methods such as urine and blood analysis, the method in accordance with the invention permits detection of exposure to an analyte over a period of time, and is therefore quite beneficial in detecting chronic drug use. Since hair is known to grow at a rate of about 0.3–0.4 mm/day or about 1.0–1.3 cm/month, it is possible to measure consumption or exposure as far back as the hair length permits by evaluating snippets of hair of various lengths, and the use of highly sensitive protein-based analytical methods permits analysis of small samples of analyte contained in the small snippets of hair.

Through sectional analysis, the method of the invention provides a relatively permanent record and evidence of a pattern of drug use, or the prior ingestion of other substances, for periods ranging from several days to months or even years after last use. The history of such exposure can be made as detailed as desired by analyzing suitably short sections of hair representing different periods of growth. In this way, prior usage over time, and the extent of such use, can be determined.

Although the use of head hair is preferred for use in the invention due to its length and accessibility, it is possible to utilize any other body hair or fingernails in the method of the invention. Thus, it is not practically possible to evade testing by the method of the invention by shaving one's head or body hair.

However, treatments such as perming and dyeing may increase the rate of digestion of hair subjected to the method according to the invention. In some cases, some analyte may be lost prior to performing the procedure due to such treatments. When the subject hair has been so altered, an increase in digestion rate is evident and an appropriate correction factor may be applied based upon known rates of normal hair digestion.

Certain other cosmetic agents, such as certain relaxing agents, may cause hair to become resistant to digestion. Such resistance may be overcome in some instances by increasing the quantity of enzyme to be used. Preferably, proteinase K is utilized as the enzyme when such resistance to digestion is encountered.

Alternatively, when it is not possible to make use of body hair or in some instance when the use of hair is not desirable, the use of other keratinized tissue such as fingernails and toenails may be used in the invention. In this regard, the effective ratio of DTT or DTE to enzyme needed to digest fingernails and toenails in order to release the analyte is about the same as for use with hair. Once the fingernail or toenail samples are digested in accordance with the method described herein, the released analyte may be analyzed by a desired analytical method.

In another aspect of the invention, it has been surprisingly discovered that melanin granules contained in hair can be dissolved by the combined action of the enzyme (preferably papain), DTT or DTE and ethylene diamine tetraacetic acid (EDTA), the latter at a concentration of about 5 mg EDTA/ ml of digest solution. Since certain analytes or drugs of abuse such as PCP have been discovered to accumulate in the granules contained in mouse hair, dissolution of the granules, which also are present in the digest solution of human hair, may possibly be effectuated and the analyte contained in the human hair granule identified.

In accordance with this aspect of the invention, a hair digest solution is obtained as described above, and the melanin granules recovered from the hair digest solution, e.g., by centrifugation. The melanin granules are then contacted with EDTA, the enzyme and DTT or DTE to release the analyte from the melanin granules, and the analyte analyzed by the methods described above.

The benefits to be obtained from use of the method according to the invention are many. The method provides a prompt and accurate diagnosis of prior exposure to a particular analyte. The subject hair and keratinized structure analysis method can provide a record of consumption, or non-consumption, over very long periods of time. Guess work regarding the true significance of one blood or urine analysis will be eliminated. Hair collection is less intrusive and less physically repulsive than blood or urine collection, and samples cannot be altered or substituted, nor can detection be evaded by short term abstention or "flushing" (excessive fluid intake) prior to a scheduled testing, e.g., pre-employment test or annual physical examination. Samples may be stored indefinitely without refrigeration.

The methods according to the invention, useful for the digestion of keratinized structures, e.g., hair, can also be used to ascertain the presence and structure of naturally occurring components of hair such as DNA.

The following examples illustrate certain aspects of the invention but they do not limit the invention as set forth in the specification and claims.

EXAMPLE 1
Extraction of Cocaine from Hair Sample 10 mg of hair was removed from a subject suspected of being a cocaine addict and washed by shaking in water at 37° C. for 30 minutes. To 10 ml. of distilled water, 110 mg. of dithiothreitol (2,3-dihydroxybutane-1,4-dithiol, Cleland's reagent, obtained from Sigma Chemical Co., St. Louis, Mo.), was added. The pH of the solution was adjusted to pH 9.1 with 15% potassium hydroxide added dropwise with stirring of the DTT solution. Stirring was continued while adding 80 microliters of Type III papain solution (papainase EC 3.4.22.2) (obtained from Sigma Chemical Co., 16-40 BAEE units activity per mg. protein). The enzyme solution was at a concentration of 30 mg of enzyme protein/ml of water, where 1 mg of enzyme protein has an activity of 16-40 BAEE units [one BAEE unit will hydrolyze 1.0 micromole of sodium benzoyl-L-arginine ethylester at pH 6.2 at 25° C.].

To 1 ml of this solution was added the 10 mg hair sample in a 13×75 mm polycarbonate test tube. The solution was incubated in a 37° C. water bath with shaking for 2 hours, and the solution was allowed to stand overnight at 37° C. without shaking. The solution containing the dissolved hair sample was centrifuged at 2,000 rpm [Damon IEC model CRU 5,000 centrifuge] to remove the melanin granules. To 1 cc of the hair digest solution was added 200 microliters of a 1 molar phosphate buffer, pH 5.5.

100 microliters of this solution was assayed by RIA for the presence of cocaine [benzoylecgonine equivalent, or "BEE"]. RIA analysis revealed 83.6 nanograms BEE/10 mg of hair.

EXAMPLE 2
Addition of Dithioerythritol

The hair sample of Example 1 was analyzed using the digestion and assay procedure set forth in Example 1, except for the replacement of dithiothreitol (DTT) by dithioerythritol (DTE). The sample was assayed by RIA, which revealed 82 nanograms cocaine (BEE) per 10 mg of hair.

EXAMPLE 3
Addition of Cupric Sulfate

After digesting the hair sample in the water bath for four hours, 100 microliters of a 10 mg/ml cupric sulfate solution was added to 1 ml of the hair digest solution prepared as set forth in Example 1. The solution was shaken at 37° C. for about 30 minutes prior to the addition of phosphate buffer and assay by RIA. One hundred microliters of the hair digest solution was subjected to RIA analysis, which revealed 85.0 nanograms of cocaine (BEE)/10 mg of hair.

EXAMPLE 4
Addition of Metal Salts to Deactivate DTT

A solution was prepared containing 100 ml water, 2.09 g BIS-Tris (Sigma Chemicals), 0.2 g cholic acid, 1.2 g dithiothreitol, and 200 units Proteinase K. The pH was adjusted to 6.5. One milliliter of the solution was then added to each 10 mg of a hair sample. After centrifugation of the digested hair, to 1.0 ml of the supernatant was added 50 µl of 1.0 M Trizma base and then 100 µl of a 1% metal salt solution (0.04 M except where indicated below). The digests were then assayed in the methamphetamine RIA.

The methamphetamine assay was performed as follows: 100 µl of the digest was placed in 12×75 mm test tube, followed by 300 µl of $^{125}$I-methamphetamine tracer and 100 µl of anti-methamphetamine (sheep) antibody. The mixture was incubated at room temperature for 1 hour at which time 200 µl of a second antibody (donkey anti-sheep) was added and the mixture incubated for another half hour. The tubes were then centrifuged for 20 minutes at about 3500 RPM. After decanting, the remaining precipitates were counted in a gamma counter.

The results in the tables below show the $B_0$'s of the digests with various metals against a control with no metal expressed as percent of the $B_0$ observed with copper sulfate, or a metal already shown to be equivalent to copper as a DTT/DTE neutralizing agent.

| METAL | $B_0$ as % of $B_0$ with Copper Sulfate in Methamphetamine Assay |
|---|---|
| EXPERIMENT 1. | |
| Copper Sulfate ($CuSO_4 \cdot H_2O$, .08 M) | 100 |
| Zinc Chloride ($ZnCl_2$, .08 M) | 111 |

-continued

| | |
|---|---|
| Cadmium Chloride (3CdSO$_4$.8H$_2$O, .08 M) | 97 |
| No Metal | 14 |
| EXPERIMENT 2. | |
| Copper Sulfate (CuSO$_4$.5H$_2$O) | 100 |
| Ferric Sulfate (Fe$_2$SO$_4$) | 98 |
| No Metal | 30 |
| EXPERIMENT 3. | |
| Copper Sulfate (CuSO$_4$.5H$_2$O) | 100 |
| Manganous Sulfate (MnSO$_4$) | 103 |
| Zinc Chloride (ZnCl$_2$) | 100 |
| No Metal | 30 |
| EXPERIMENT 4. | |
| Copper Sulfate (CuSO$_4$.5H$_2$O) | 100 |
| Mercuric Chloride (HgCl$_2$) | 80 |
| Silver Nitrate (AgNO$_3$) | 86 |
| Cobalt Chloride (CoCl$_2$.6H$_2$O) | 68 |
| No Metal | 30 |

| METAL | $B_o$ as % of $B_o$ with Cadmium Chloride in Methamphetamine Assay |
|---|---|
| EXPERIMENT 5. | |
| Cadmium Chloride (3CdSO$_4$.8H$_2$O) | 100 |
| Lead Nitrate (Pb(NO$_3$)$_2$) | 107 |
| Lead Acetate (Pb(Ac)$_2$.3H$_2$O) | 110 |
| No Metal | 45 |

| METAL | $B_o$ as % of $B_o$ with Ferric Sulfate in Methamphetamine Assay |
|---|---|
| EXPERIMENT 6. | |
| Ferric Sulfate (Fe$_2$SO$_4$) | 100 |
| Manganous Sulfate (MnSO4) | 100 |
| Ferrous Chloride (FeCl$_2$.4H$_2$O) | 95 |
| Ferric Chloride (FeCl$_3$) | 98 |
| Ferric Chloride (FeCl$_3$.6H$_2$O) | 96 |
| Ferric Sulfate (Fe$_2$SO$_4$.7H$_2$O) | 99 |
| No Metal | 29 |

EXAMPLE 5
Addition of Sodium Arsenite

After digesting the hair sample in the water bath for four hours, 100 microliters of a 100 mg/ml sodium arsenite solution was added to 1.0 ml of the hair digest solution prepared as set forth in Example 1. The solution was shaken at 37° C. for 30 minutes. 200 microliters of 1M, pH 6.5, phosphate buffer was added prior to assay by RIA. A precipitate was observed. One hundred microliters of the hair digest solution was subjected to RIA analysis, which revealed 82 nanograms of cocaine (BEE) per 10 mg of hair.

EXAMPLE 6
Substrate Activation by Dithiothreitol (DTT)

10 mg of hair were exposed to 11 mg of DTT at pH 9.1 for a period of 20 hours. The DTT solution was removed and replaced with DTT and papain as in EXAMPLE 1. The hair specimen dissolved within 10 minutes as compared to within one hour for a control specimen not pretreated with DTT and digested as in EXAMPLE 1, thereby demonstrating that DTT activated not only the sulfhydryl-dependent enzyme, papain, but the enzyme substrate, hair, as well.

EXAMPLE 7
Digestion of Fingernails

A 10 mg. sample of fingernail clippings was obtained from a subject, and subjected to a detergent wash. 220 mg of DTT was added to 10 ml of water in a test tube and the pH adjusted to pH 9.1 as in Example 1. A papain suspension, 160 microliters, was then added. 1.0 ml of this solution was then added in a test tube to 10 mg of fingernail clippings and shaken at 37° C. for a period of 24 hours until dissolution occurred. The digest solution was then analyzed by RIA as previously described.

EXAMPLE 8
Performance of Sectional Analysis

A hair sample, about 6 cm in length, was obtained from an individual suspected of being a heroin addict. The samples were carefully sectioned into three 2 cm sections, with corresponding sections added to three separate test tubes and washed. The hair samples were subjected to the process described in Example 1, except that chymopapain (EC 3.4.22.6) was used in place of papain as the enzyme. The samples were agitated overnight as previously described.

RIA analysis revealed morphine content in the three sections of 13.5, 5.7 and 0 nanograms/10 mg hair.

EXAMPLE 9
Digestion of Digestion-Resistant Hair

Ten milligrams of hair which had been treated with relaxer was incubated overnight in the solution digest described in Example 6. The hair sample did not dissolve in the usual 20-hour period. A greater and additional amount of proteinase K, i.e., 1 mg, was then added to the partially digested sample. The sample then dissolved within the next 24 hours. The digest was centrifuged and 100 $\mu$l CuSO$_4$ solution (10 mg/ml) was added to 1 ml of the supernatant which was then shaken at 37 degrees centigrade for 30 minutes. 200 $\mu$l of 1 M phosphate buffer pH 7 was added. Due to the high amount of proteinase K in the resulting digest, 20 $\mu$l of the inhibitor phenylmethyl sulfonyl chloride in ethanol was added to the digest prior to assay by RIA.

RIA analysis revealed 7.4 ng cocaine/10 mg hair.

EXAMPLE 10
Digestion and Analysis of Hair Using Proteinase K and Cholic Acid Detergent Separate samples of 10 mg of normal hair and 10 mg of hair containing the cocaine metabolite benzoylecgonine (BEE) were collected and placed in separate 12×75 mm polycarbonate tubes. One ml of the following solution was added to the hair in each of the tubes: 0.5M Tris buffer (pH 6.5 at room temperature) containing one ml 2 U Proteinase K, 20 mg cholic acid (sodium salt) and 60 mg dithiothreitol. The mixtures were shaken 16 hours at 37° C. After 16 hours, the samples were centrifuged at 3,000 RPM for 20 minutes. To 0.9 ml of the supernatant removed after centrifugation was added 10 $\mu$l of phenylmethylsulfonyl fluoride (6% in Ethanol). This was mixed, followed by the addition of 90 $\mu$l CuSO$_4$.5H$_2$O (10 gm/liter) to each solution. This mixture was shaken at 37° C. for 30 minutes. 100 $\mu$l of this mixture was then assayed by RIA. Equivalent solutions as described but containing no cholic acid detergent and no hair protein were also assayed. The results were as follows:

A. Sample of hair protein not containing cholic acid or BE:
  14,686 cpm (counts per minutes on gamma counter) ($B_O$).
  100 $\mu$l sample of hair protein containing 0.14 ng BE and no cholic acid: 11,128 cpm (B), or a $B/B_O$ of 76% (indicating the presence of BE).

B. 100 μl sample of hair containing cholic acid but no BE: 12,048 cpm ($B_O$)

100 μl sample of hair containing 0.14 ng BE and cholic acid: 8,602 cpm (B), or a $B/B_O$ of 71% (indicating presence of BE)

The similarity of the resulting $B/B_O$'s (76% and 71%) with and without cholic acid indicate that cholic acid did not interfere with the assay for cocaine or benzoylecgonine.

EXAMPLE 11

Digestion of Hair Using Proteinase K and Removal of Interfering Substance in Marijuana Assay 10 mg of hair from a known normal subject (not marijuana users) and 10 mg of hair from 1 known marijuana user were placed in separate 13×75 mm polycarbonate tubes. One ml of the following solution was added to the hair in each of the tubes: 0.5M Tris buffer (pH 6.5 at room temperature) containing in one ml 2 U Proteinase K, 2 mg cholic acid (sodium salt), and 60 mg dithiothreitol. The mixtures were shaken 16 hours at 37° C. After 16 hours, the samples were centrifuged at 3,000 RPM for 20 minutes. To 0.9 ml of supernatant removed after centrifugation was added 10 μl of phenylmethylsulfonyl fluoride (6% in ethanol). This was mixed, followed by the addition of 90 μl $CuSO_4.5H_2O$ (10 gm/liter). The mixtures were shaken at 37° C. for 30 minutes.

Six grams of dry A-25-120 DEAE Sephadex® available from Sigma Chemical Co. of St. Louis, Mo., was added to 100 ml of distilled, deionized water. The suspension was allowed to swell overnight in the refrigerator (2–8° C). After swelling, the suspension was placed in a beaker with a large magnetic stirring bar, and was vigorously stirred on a magnetic stirring plate for 60 minutes until the resin had broken up into small particles resulting in a very fine suspension.

To 400 μl of each of the hair digest solutions was added 300 μl of the 6% resin suspension in a glass tube. The glass tubes were rotated vigorously (greater than 200 rotations/minute) for 30 minutes in such a way as to keep the resin suspended and in contact with the digest solution. To each of the tubes was added 0.7 ml distilled water. The tubes were then centrifuged, and 1.0 ml of the supernatant from the resinated digest solutions was removed. 200 μl of 1M phosphate buffer was then added to each solution. 100 μl of the filtrate of each sample was then assayed for marijuana by RIA. The results were as follows:

Sample 1 (known negative) 4597 cpm

Sample 2 (known positive) 2683 cpm

Sample 2 demonstrated a $B/B_O$ of 59% as compared to negative samples (100%), a positive result for the presence of marijuana analyte in Sample 2.

EXAMPLE 12

Known Negative Hair Samples Compared to Known Positive Hair Samples Using Ion Exchange Resin Eight negative hair samples known to show great variability in binding in the marijuana assay due to varying amounts of interfering cross reacting substance, and a hair sample from a known marijuana user were digested and neutralized by the procedure described in Example 10. The digests were treated with water suspensions of various resins prepared in the concentrations (as percent of bottled resin relative to total suspension) shown below and the resinated digest solution was then tested in RIA.

In more detail, 0.4 ml of the digest solution was mixed 0.3 ml of the resin suspension in a 13×100-mm glass tube, and the tubes were shaken at >200 rpm for 30 minutes. Then 0.75 ml of distilled water was added to each of the tubes, and the tubes were mixed well and centrifuged at 200 RPM for 10 minutes. One ml of supernatant was removed from each and placed in a 13×100 mm glass tube.

In performing the marijuana assay, 200 μl of 1 M, pH 7 phosphate buffer was added to the tube, followed by 100 μl $I^{125}$ marijuana tracer and 100 μl anti-cannabinoid antibody. The tubes were mixed and incubated 1 hour at room temperature. 200 μl of a second precipitating antibody was added followed by 1 ml 6% polyethylene glycol. After 30 minutes at room temperature, the tubes were centrifuged at 3000 RPM in a refrigerated centrifuge. After decanting, the tubes were counted in a gamma spectrometer.

The means and standard deviations of the counts of the negatives were calculated to determine the effectiveness of the resin in removing the interfering crossreactor substance. The counts of the positive hair sample digest divided by the mean of negatives was calculated to determine how well the analyte was not removed.

The following results were obtained using a 2.4% resin suspension of DEAE-Sephadex® (A-50-120):

| Sample | CPM |
| --- | --- |
| Negative #1 | 3961 |
| Negative #2 | 4391 |
| Negative #3 | 3712 |
| Negative #4 | 3804 |
| Negative #5 | 3574 |
| Negative #6 | 4004 |
| Negative #7 | 4010 |
| Negative #8 | 4252 |
| Positive #1 | 2489 |
| Positive #2 | 2424 |

The mean of the negative samples was 3964, with a standard deviation of 238 (6% of the mean). The $B/B_O$ of the positive samples is 62%. Thus, the signal to noise ratio indicates that the assay is sensitive.

For DEAE Sepharose® (CL-6B), the following 5 results were obtained using a 24% resin suspension:

| Sample | CPM |
| --- | --- |
| Negative #1 | 4085 |
| Negative #2 | 4070 |
| Negative #3 | 3661 |
| Negative #4 | 3771 |
| Negative #5 | 3555 |
| Negative #6 | 3677 |
| Negative #7 | 3806 |
| Negative #8 | 4137 |
| Positive #1 | 2550 |
| Positive #2 | 2539 |

The mean of the negative samples was 3845, with a standard deviation of 196 (5% of the mean). The $B/B_O$ is 66%. Thus, again, the signal to noise ratio indicates that the assay is sensitive.

While there have been described what are presently believed to be preferred embodiments of the invention, it will be apparent to one skilled in the art that numerous changes can be made in the ingredients, conditions and proportions set forth in the foregoing embodiments without departing from the invention as described herein and as defined in the appended claims.

What is claimed is:

1. A method for the detection and identification of an organic analyte from the bloodstream of a subject which becomes embedded in a keratinized structure of the subject which comprises:
    (a) preparing a mixture comprising an enzyme suitable for digestion of the keratinized structure, an agent selected from the group consisting of dithiothreitol and dithioerythritol, and a sample of the keratinized structure;
    (b) permitting the digestion of the sample; and
    (c) subjecting a portion of the mixture to direct analysis by immunoassay to determine whether an organic analyte is present in the sample.

2. The method according to claim 1 wherein the keratinized structure is hair.

3. The method according to claim 1 wherein the pH at which the method is performed is between about 6 and 8.

4. A method for the detection and identification of an organic analyte from the bloodstream of a subject which becomes embedded in the hair of the subject which comprises:
    (a) preparing a mixture comprising an enzyme suitable for digestion of the hair, an agent selected from the group consisting of dithiothreitol and dithioerythritol, and a sample of the hair;
    (b) permitting the digestion of the sample; and
    (c) subjecting a portion of the mixture to direct analysis by immunoassay to determine whether an organic analyte is present in the sample.

* * * * *